United States Patent
Schafer

(10) Patent No.: US 7,632,264 B2
(45) Date of Patent: Dec. 15, 2009

(54) MEDICAL TOOLS FOR DENTAL TREATMENTS BY MEANS OF A LASER

(76) Inventor: Olaf Schafer, Hittisheimerstrasse 18d, 78224 Singen (DE)

( * ) Notice: Subject to any disclaimer, the term of this patent is extended or adjusted under 35 U.S.C. 154(b) by 484 days.

(21) Appl. No.: 10/516,656

(22) PCT Filed: Jun. 10, 2003

(86) PCT No.: PCT/EP03/06084

§ 371 (c)(1),
(2), (4) Date: Nov. 30, 2004

(87) PCT Pub. No.: WO03/103529

PCT Pub. Date: Dec. 18, 2003

(65) Prior Publication Data

US 2005/0170310 A1  Aug. 4, 2005

(30) Foreign Application Priority Data

Jun. 10, 2002 (DE) .............................. 102 25 749

(51) Int. Cl.
*A61B 18/20* (2006.01)
*A61C 1/00* (2006.01)

(52) U.S. Cl. ................................ 606/13; 606/3; 433/29
(58) Field of Classification Search ................ 606/3, 606/13–19, 22; 433/29
See application file for complete search history.

(56) References Cited

U.S. PATENT DOCUMENTS

| | | | | | |
|---|---|---|---|---|---|
| 5,540,676 | A | * | 7/1996 | Freiberg | 606/3 |
| 5,971,755 | A | * | 10/1999 | Liebermann et al. | 433/29 |
| 6,083,218 | A | * | 7/2000 | Chou | 606/10 |
| 6,129,721 | A | * | 10/2000 | Kataoka et al. | 606/2 |
| 6,350,123 | B1 | * | 2/2002 | Rizoiu et al. | 433/80 |
| 6,835,064 | B2 | * | 12/2004 | Burtscher et al. | 433/29 |
| 7,040,892 | B2 | * | 5/2006 | Hirszowicz et al. | 433/29 |
| 7,144,248 | B2 | * | 12/2006 | Irwin | 433/29 |

* cited by examiner

*Primary Examiner*—Ahmed M Farah
(74) *Attorney, Agent, or Firm*—Bachman & LaPointe, P.C.

(57) ABSTRACT

A medical tool for dental treatments by means of a laser, the light guide of which runs in a hand piece. The light guide is provided with a laser module including power circuitry and a second laser module is provided with the first laser module, operating at a different wavelength.

6 Claims, 2 Drawing Sheets

MEDICAL TOOLS FOR DENTAL TREATMENTS BY MEANS OF A LASER

BACKGROUND OF THE INVENTION

The present invention relates to a medical tool for dental treatments by means of a laser, whose light guide runs in a handpiece, said light guide being assigned a laser module with power circuitry.

In the field of dentistry, there are presently five different laser types with a total of seven different wavelengths. For example, a dental laser with a handpiece is disclosed in WO 93/19684. With such a laser, however, only a single method of treatment is possible. The same applies also to a medical tool corresponding to EP 0 523 506 A1, in which channels for a coolant are also provided in the handpiece.

DE 198 44 719 A1 discloses a laser treatment device, in particular for performing medical or surgical treatment by means of laser radiation. This device comprises a solid-state laser for generating a laser beam, an excitation light source which excites the solid-state laser, a first optical system with a Q-switch which transmits light waves generated by the solid-state laser as a pulsed laser beam, a second optical system with which light waves generated by the solid-state laser are transmitted as a continuous wave laser, and a system for switching the optical path, with which system an optical path for the light oscillations generated by the solid-state laser is switched from one of the optical paths of the first optical system or of the second optical system.

In U.S. Pat. No. 6,270,342 B1, a handpiece specially designed for dental treatments is proposed. The handpiece contains a functional device which, for example, can be a diode laser, a diode-pumped solid-state laser, an LED, a microwave generator or ultrasound generator. In an illustrative embodiment 6, it is then stated that light from the laser device can be divided into two light systems. The first laser system is used for the surgical intervention, and the second laser system disinfects the tissue in order to reduce side effects or blood loss.

The object of the present invention is to develop a medical device of the above-mentioned type which allows the dentist to use one and the same device to carry out different treatments in dentistry.

SUMMARY OF THE INVENTION

The foregoing object is achieved by the present invention wherein the first laser module is assigned a second laser module with a different wavelength.

Especially when a short-wavelength laser is chosen for the first laser module and a long-wavelength laser is chosen for the second laser module, about 90 to 95% of all desired treatments can be performed with one and the same tool. This affords clear advantages for the dentist, encouraging him to invest in a tool of this kind.

In a preferred illustrative embodiment, the first module should be one for a diode laser, a wavelength of 750 to 1100 nm being preferred. More restrictively, the wavelength preferably lies at 810±10 nm or 980±10 nm. The power is typically from 1 to 20 W.

The second, long-wavelength laser is preferably an erbium:YAG laser in a wavelength range of 2500 to 3500 nm. Here, a wavelength of 2940±100 nm is preferred.

It is conceivable to assign the same light guide to both laser modules. However, the illustrative embodiment is preferred in which each laser module has its own light guide, it being possible to provide both light guides together in one handpiece or else separately in separate handpieces. For the diode laser, glass fiber is preferred as the light guide, and a hollow waveguide is preferred for the erbium:YAG laser.

The diode laser should preferably also be assigned an optical element composed of two lenses. Moreover, a line for a coolant is also provided in the handpiece.

As has been mentioned above, the different lines can be provided in a single handpiece, but it is also conceivable for the dentist to have several handpieces available with different combinations of light guide and/or coolant line. The latter has the advantage that the dentist cannot inadvertently start up incorrect operations since he always has to select the desired handpiece and he does not inadvertently trigger undesired functions via the wrong switch.

The handpiece should preferably be connected in a releasable manner to a rear part which in turn communicates with a base unit via a common line. The laser modules, the associated power circuitry and control modules are housed together in this base unit. The base unit can also have a display and/or touch screen with which the dentist can select defined functions.

BRIEF DESCRIPTION OF THE DRAWINGS

Further advantages, features and details of the invention will become clear from the following description of preferred illustrative embodiments and from the drawing, in which.

DETAILED DESCRIPTION

Figure 1:
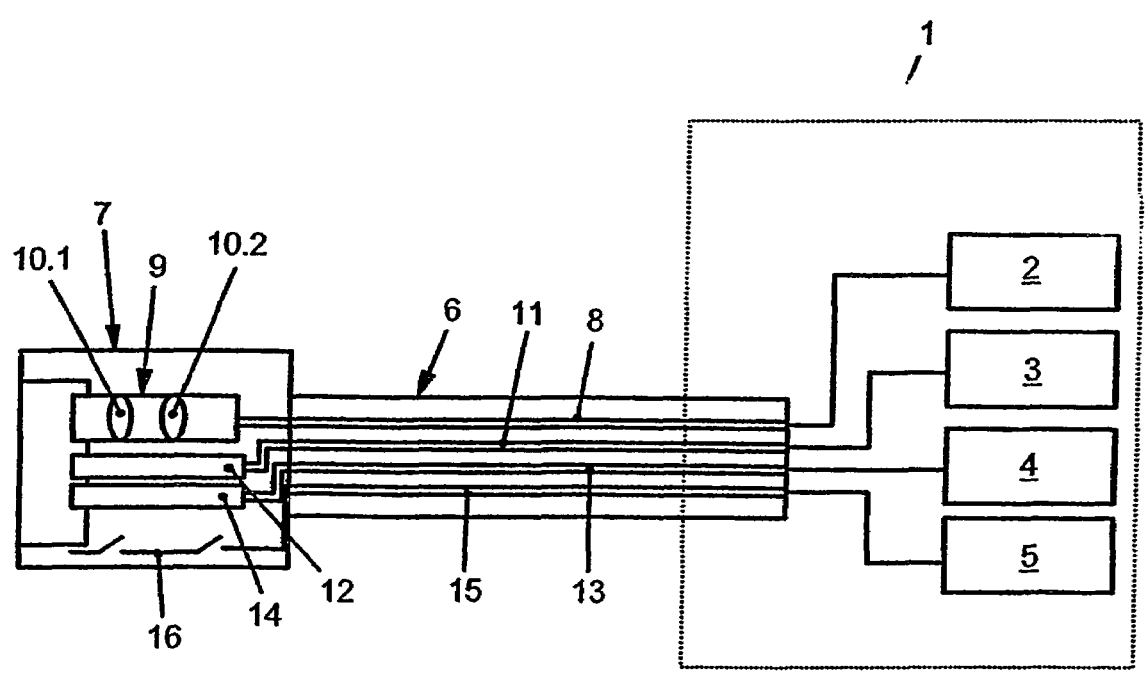
FIG. 1 shows a plan view, in block diagram form, of part of the medical tool according to the invention for dental treatments by means of a laser.

According to FIG. 1, a laser module 2 of a diode laser and a laser module 3 of an erbium:YAG laser are accommodated in a base unit 1. A source 4 for coolant, and control circuitry 5, are also provided.

The base unit 1 is in communication with a rear part 7 via a common line 6. The diode laser module 2 is connected via a connection line 8 to an optical element 9 in which two lenses 10.1 and 10.2 are fitted.

The erbium:YAG laser 3 is connected via a connection line 11 to a hollow waveguide 12 which preferably has a stainless steel tube in which the laser light is reflected.

A connection line 13 from the source 4 for coolant opens into a transfer piece 14. A connection line 15 from the control circuitry 5 is in communication with switch elements 16 for function selection.

Figure 2:
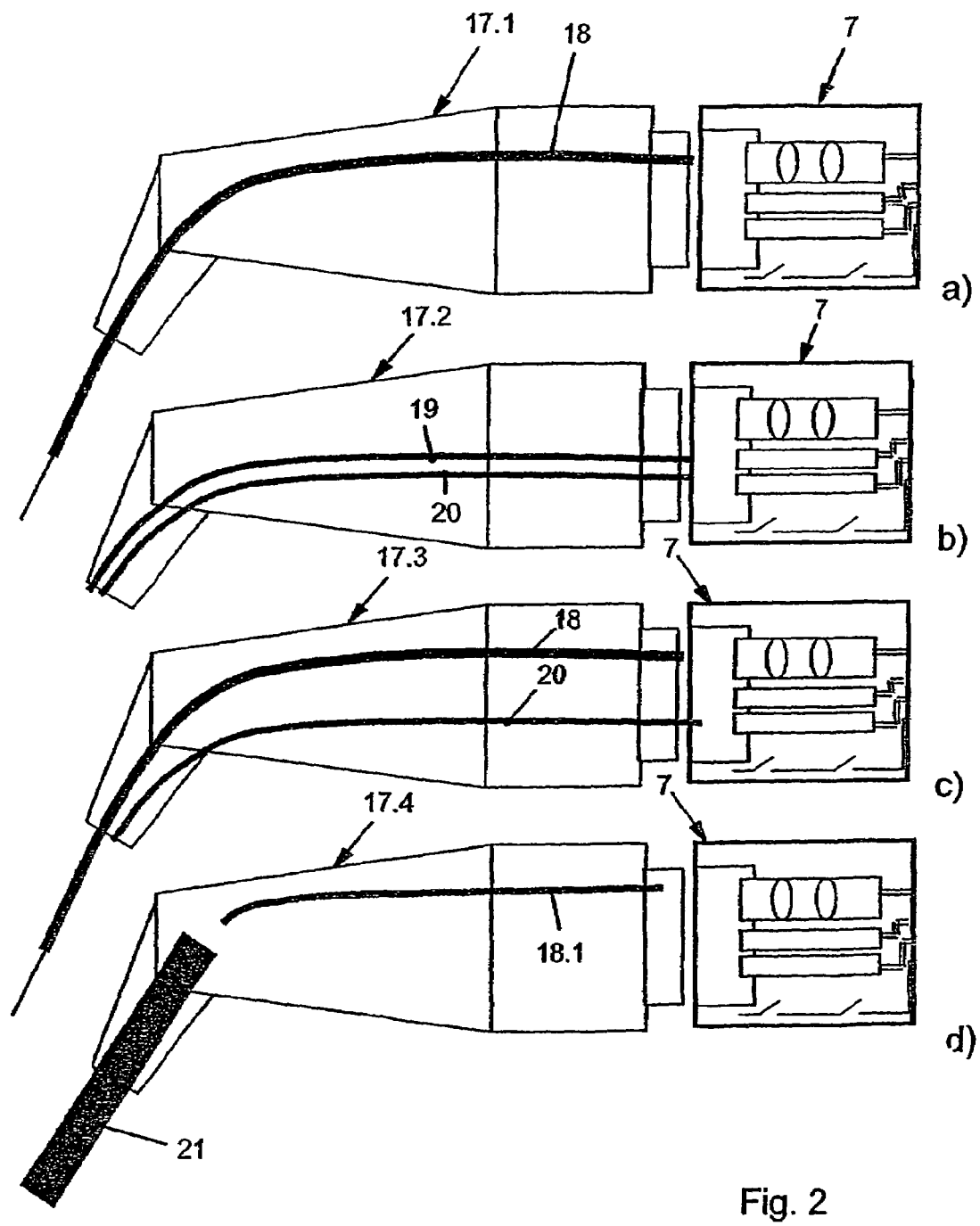
FIGS. 2(a) to (d) show schematic plan views of other parts of the medical tool for dental treatments by means of a laser.

According to FIG. 2, different handpieces can be fitted into the rear part 7. The handpiece 17.1 of FIG. 2(a) is suitable for general operation of a diode laser and therefore has only a light guide 18. This diode laser should have a high power, typically of from 3 to 20 W.

A light guide 19 for the erbium:YAG laser and a coolant line 20 are integrated in a handpiece 17.2 according to FIG. 2(b).

By contrast, in a handpiece 17.3 according to FIG. 2(c), the light guide 18 for the diode laser is combined with the coolant line 20.

In the handpiece 17.4 according to FIG. 2(d), the laser concerned is a soft laser with low power, ca. 100 mW, in which a light guide 18.1 is assigned a large surface area glass rod 21 which can have a diameter of 5 to 8 mm. This can be used in particular for gentle treatment of larger dental areas.

The mode of functioning of the present invention is as follows:

The base unit 1 with the corresponding laser modules 2 and 3, the source 4 for coolant and the control circuitry 5, stands next to a treatment chair. The dentist providing the treatment has the rear part 7 connected via the common line 6 to the base unit 1. To treat a patient, he can now select a suitable handpiece 17.1 to 17.4 from a set available to him, depending on what kind of treatment he wishes to perform on the patient. He can set up the appropriate light guides 18, 18.1, 19 and coolant lines 20 via the switch elements 16 on the rear part 7. Of course, this can also be done via a suitable foot switch.

The invention claimed is:

1. A medical tool for dental treatment comprising:
a base unit, said base unit includes (1) a laser module of a diode laser, (2) a laser module of an erbium:YAG laser, (3) a coolant source, and (4) control circuitry;
a rear unit connected to the base unit via a common line, said rear unit includes (1) an optical element, (2) a hollow waveguide, (3) a transfer piece, and (4) switch elements for function selection; and said common line comprises (1) a first connection line connecting the laser module of a diode laser to the optical element, (2) a second connection line connecting the laser module of an erbium:YAG laser to the hollow waveguide, (3) a third connection line connecting the coolant source to the transfer piece, and (4) a fourth connection line for connecting the control circuitry to the switch elements for further selection; and
a plurality of separate handpieces selectively fittable to the rear unit, wherein each of said plurality of separate handpieces includes at least one of the following:
(a) a light guide connectable to the first connection line for the diode laser;
(b) a light guide connectable to the second connection line for the erbium:YAG laser; and
(c) a coolant line connectable to the third connection line for the coolant source;
wherein a single handpiece is selected from the plurality of separate handpieces and secured to the rear unit depending on treatment to be performed.

2. The tool as claimed in claim 1, wherein the laser module of the diode laser has a wavelength of 750 to 1100 nm and a power of 1 to 10 W.

3. The tool as claimed in claim 2, wherein the laser module of the erbium:YAG laser is a long-wavelength erbium:YAG laser.

4. The tool as claimed in claim 3, wherein the wavelength of the erbium:YAG laser is between 2500 to 3500 nm.

5. The tool as claimed in claim 4, wherein the hollow waveguide comprises a stainless steel tube.

6. The tool as claimed in claim 5, wherein the optical element comprises at least two lenses.

* * * * *

UNITED STATES PATENT AND TRADEMARK OFFICE
CERTIFICATE OF CORRECTION

PATENT NO. : 7,632,264 B2                                        Page 1 of 1
APPLICATION NO. : 10/516656
DATED           : December 15, 2009
INVENTOR(S)     : Olaf Schafer It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 572 days.

Signed and Sealed this

Twenty-first Day of December, 2010

David J. Kappos
*Director of the United States Patent and Trademark Office*